(12) United States Patent
Vase

(10) Patent No.: US 9,149,632 B1
(45) Date of Patent: Oct. 6, 2015

(54) IMPLANTABLE MEDICAL DEVICES IMAGING FEATURES

(75) Inventor: Abhi Vase, San Jose, CA (US)

(73) Assignee: Pacesetter, Inc., Sylmar, CA (US)

( * ) Notice: Subject to any disclaimer, the term of this patent is extended or adjusted under 35 U.S.C. 154(b) by 1974 days.

(21) Appl. No.: 11/830,663

(22) Filed: Jul. 30, 2007

(51) Int. Cl.
*A61N 1/05* (2006.01)

(52) U.S. Cl.
CPC ............. *A61N 1/057* (2013.01); *A61N 1/0573* (2013.01)

(58) Field of Classification Search
CPC ............................ A61N 1/057; A61N 1/0573
USPC .................... 607/63, 116, 122, 127; 600/434
See application file for complete search history.

(56) References Cited

U.S. PATENT DOCUMENTS

| | | | | |
|---|---|---|---|---|
| 4,026,303 | A * | 5/1977 | Babotai | 607/127 |
| 6,493,591 | B1 * | 12/2002 | Stokes | 607/127 |
| 7,212,870 | B1 * | 5/2007 | Helland | 607/127 |
| 2003/0097064 | A1 * | 5/2003 | Talpade et al. | 600/434 |
| 2003/0144718 | A1 | 7/2003 | Zeijlemaker | |
| 2003/0144719 | A1 | 7/2003 | Zeijlemaker | |
| 2004/0111139 | A1 * | 6/2004 | McCreery | 607/117 |
| 2008/0294229 | A1 * | 11/2008 | Friedman et al. | 607/127 |

FOREIGN PATENT DOCUMENTS

| | | |
|---|---|---|
| WO | WO03/063952 A2 | 8/2003 |
| WO | WO03/063952 A3 | 8/2003 |
| WO | WO03/063957 A2 | 8/2003 |
| WO | WO03/063957 A3 | 8/2003 |

OTHER PUBLICATIONS

Ciocan, Razvan et al., "A Transmission Line Matrix Model for Shielding Effects in Stents," Proc. EHE Conf. 2006:1.129-1.134 (Portugal).
Klemm M.D., Thomas et al., "MR Imaging in the Presence of Vascular Stents: A Systematic Assessment of Artifacts for Various Stent Orientations, Sequence Types,and Field Strengths," J. Magn. Reson. Imaging 2000;12:606-615.
Edelstein, W.A. et al., "Active-Passive Gradient Shielding for MRI Acoustic Noise Reduction," Proc. Intl. Soc. Mag. Reson. Med. 2004;11.
Van Holten, Jacqueline et al., "High Flip Angle Imaging of Metallic Stents: Implications for MR Angiography and Intraluminal Signal Interpretation," Magn Reson Med 2003;50:879-883.

* cited by examiner

*Primary Examiner* — Christopher D Koharski
*Assistant Examiner* — Michael D Abreu

(57) ABSTRACT

Exemplary techniques, devices, and systems relating to implantable medical devices (IMDs) and IMD features pertaining to imaging and charge induction are described. One IMD includes means for receiving a first signal relating to a magnetic resonance imaging process. The IMD further includes means for generating a second signal effective to reduce or cancel charge induced upon a lead of the IMD by the magnetic resonance imaging process.

8 Claims, 8 Drawing Sheets

IMPLANTABLE MEDICAL DEVICES IMAGING FEATURES

FIELD OF THE INVENTION

The subject matter presented herein generally relates to implantable medical devices (IMDs) and IMD imaging features.

BACKGROUND

Current implantable medical devices (IMDs) such as cardiac pacemakers and defibrillators include components that are prone to heating and/or charge induction upon exposure to strong magnetic fields. Conditions within an operating magnetic resonance imaging (MRI) machine offer an example of such strong magnetic fields. For instance, activation of the MRI's radio frequency (rf) coil generates rf pulses that can induce charge and/or cause heating on the IMD. Charge induction and/or heating of the IMD can cause patient discomfort, damage to patient tissue, and/or diminished IMD efficacy, among other consequences.

SUMMARY

Exemplary techniques, devices, and systems relating to implantable medical devices (IMDs) and IMD features pertaining to imaging and charge induction are described. One IMD includes means for receiving a first signal relating to a magnetic resonance imaging process. The IMD further includes means for generating a second signal effective to reduce or cancel charge induced upon a lead of the IMD by the magnetic resonance imaging process.

Another IMD includes a control unit for processing signals and a lead coupled to the control unit. The lead includes a conductive mechanism operable to deliver the signals between the control unit and a target tissue. The lead further includes an imaging-related mechanism to enhance imaging of the lead and to reduce charge induced upon the conductive mechanism during imaging.

BRIEF DESCRIPTION OF THE DRAWINGS

Features and advantages of the described implementations can be more readily understood by reference to the following description taken in conjunction with the accompanying drawings. In the description that follows, like numerals or reference designators will be used to reference like parts or elements wherever feasible.

DETAILED DESCRIPTION

Overview

Various exemplary techniques, methods, devices, systems, etc., described herein pertain to implantable medical devices (IMD) and IMD designs that address imaging considerations such as image resolution and/or charge induction. Magnetic resonance imaging (MRI) is a widely used tool for non-invasively rendering internal images of a patient. MRIs are often useful for determining a condition of patients who have IMDs, such as implantable cardiac pacing/defibrillation devices. Imaging various IMD components, such as leads, at a desired resolution can be difficult. Some of the described implementations have features that can enhance lead resolution in the magnetic resonance imaging process. For instance, one implementation employs image enhancing structures, such as coils, in the lead to enhance imaging resolution. Further, a radio frequency signal or pulses generated by the MRI during the magnetic resonance imaging process can induce charge upon the leads. The induced charge can cause patient discomfort and/or tissue damage due to heating. Various implementations have features that can reduce or cancel the induced charge on the lead and thereby reduce the resultant affects on patient tissues. For instance, some implementations generate a signal to effectively reduce or cancel the rf inductive affects resulting from the magnetic resonance imaging process on the IMD. Still other implementations employ various mechanisms to address the affects of the rf pulses. In some cases, induction reducing mechanisms are employed to reduce charge induction. Other implementations employ self-cancelling conductive pathways for delivering signals from an IMD control unit to an electrode positioned proximate a target tissue. The self-cancelling conductive pathways can address rf affects on the lead.

Exemplary IMD

The techniques and devices described below can be implemented in relation to any implantable medical device (IMD) that is configured or configurable to sense cardiac data and/or to provide cardiac therapy.

Figure 1:
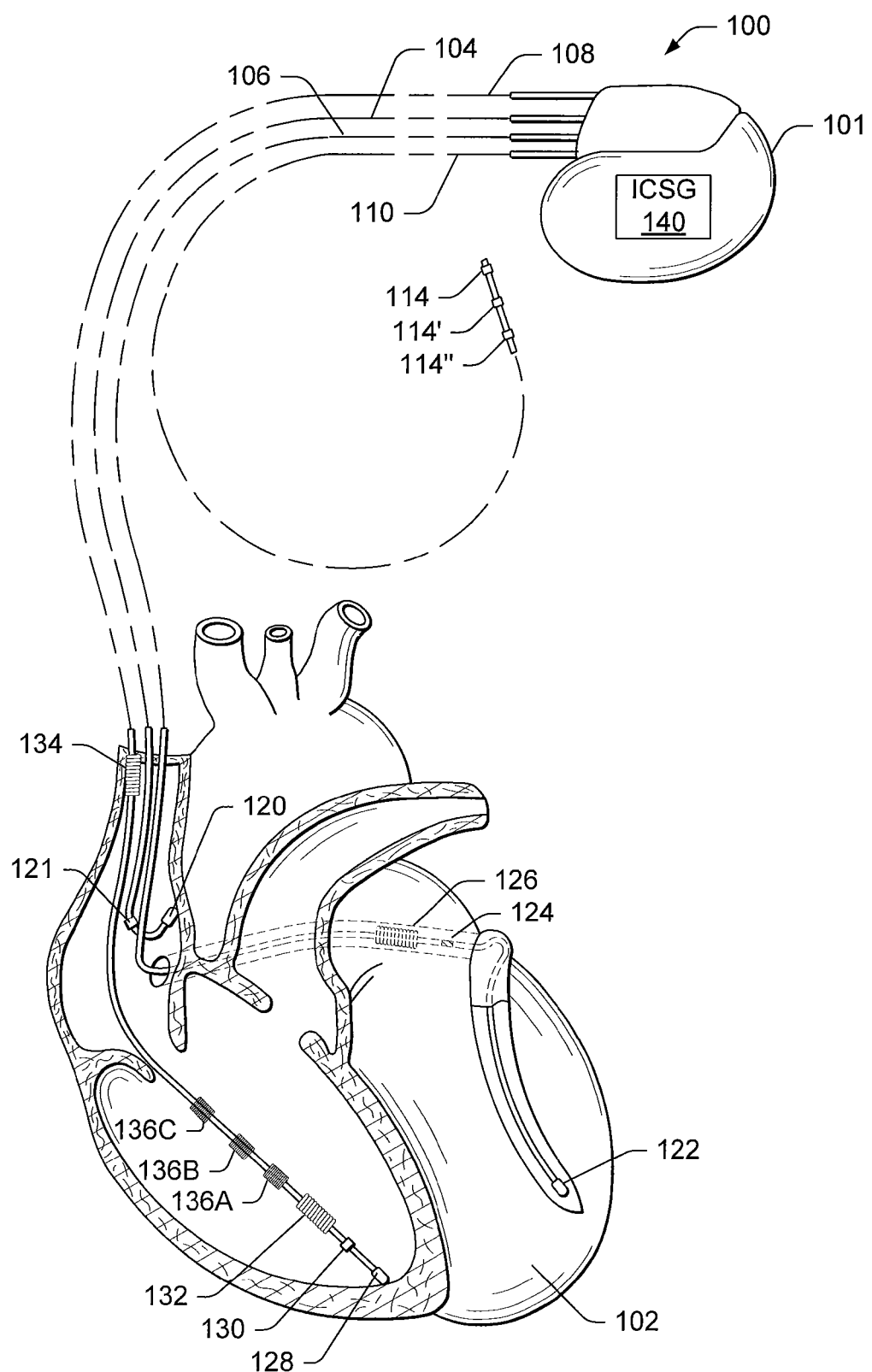
FIG. 1 is a simplified diagram illustrating an exemplary implantable medical device (IMD) operable to address imaging and/or charge induction in accordance with one implementation.

FIG. 1 shows an exemplary IMD 100 suitable for delivering multi-chamber stimulation and shock therapy. IMD 100 includes a control unit 101 that is in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves, non-myocardial tissue, other nerves, etc. In addition, IMD 100 includes a fourth lead 110 having, in this implementation, three electrodes 114, 114', 114" suitable for stimulation of autonomic nerves, non-myocardial tissue, other nerves, etc. For example, this lead may be positioned in and/or near a patient's heart or near an autonomic nerve within a patient's body and remote from the heart. In another example, the fourth lead can be configured to sense the phrenic nerve and/or activation of the diaphragm. The right atrial lead 104, as the name implies, is positioned in and/or passes through a patient's right atrium. The right atrial lead 104 optionally senses atrial cardiac signals and/or provides right atrial chamber stimulation therapy. As shown in FIG. 1, the IMD 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves, non-myocardial tissue, other nerves, etc. In an alternative configuration, lead 110 can be replaced with a mechanism for connecting the IMD to various other devices. For example, the mechanism can facilitate connecting IMD 100 to a drug pump for dispensing drugs into the patient in accordance with instructions received from the IMD. The skilled artisan should recognize various other configurations that may be employed which are consistent with the principles described above and below.

To sense atrial cardiac signals, ventricular cardiac signals and/or to provide multi-site pacing therapy, particularly on the left side of a patient's heart, the IMD 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

IMD 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

The right ventricular lead (and/or other leads) may alternatively or additionally include one or more imaging electrodes. In this example, three imaging electrodes 136A, 136B, and 136C are included on RV lead 108. In this case, imaging electrodes 136A, 136B, and 136C are manifest as coil electrodes and can enhance image resolution of RV lead 108 during imaging as will be described in more detail below. Alternatively or additionally, imaging electrodes 136A, 136B, and 136C can reduce tissue damage proximate tip electrode 128, by reducing heat transfer into the right ventricular tissue proximate the RV tip electrode during imaging. Imaging electrodes 136A, 136B, and 136C are positioned in a large volume of blood in the right ventricle that readily dissipates heat when compared to cardiac tissue contacting tip electrode 128.

In an imaging scenario employing a magnetic resonance imaging (MRI) machine, IMD 100 is exposed to a relatively large magnetic field and radio frequency (rf) pulses. For instance, MRI machines currently employed in medical scenarios often utilize 1.5-3.0 tesla magnets. Other magnet strengths may be employed as MRI technologies continue to mature. During patient imaging, the magnetic field and/or the rf pulses can induce charges upon one or more of leads 104-110. IMD 100 addresses charge induction via an induction-cancelling signal generator (ICSG) module 140. The induction-canceling signal generator 140 causes a signal to be generated for delivery to one or more of leads 104-110 to reduce and/or cancel charge induction upon the leads related to exposure to the magnetic field and/or rf pulses. This and other techniques and devices are described below to address charge induction upon the IMD leads.

Figure 2:
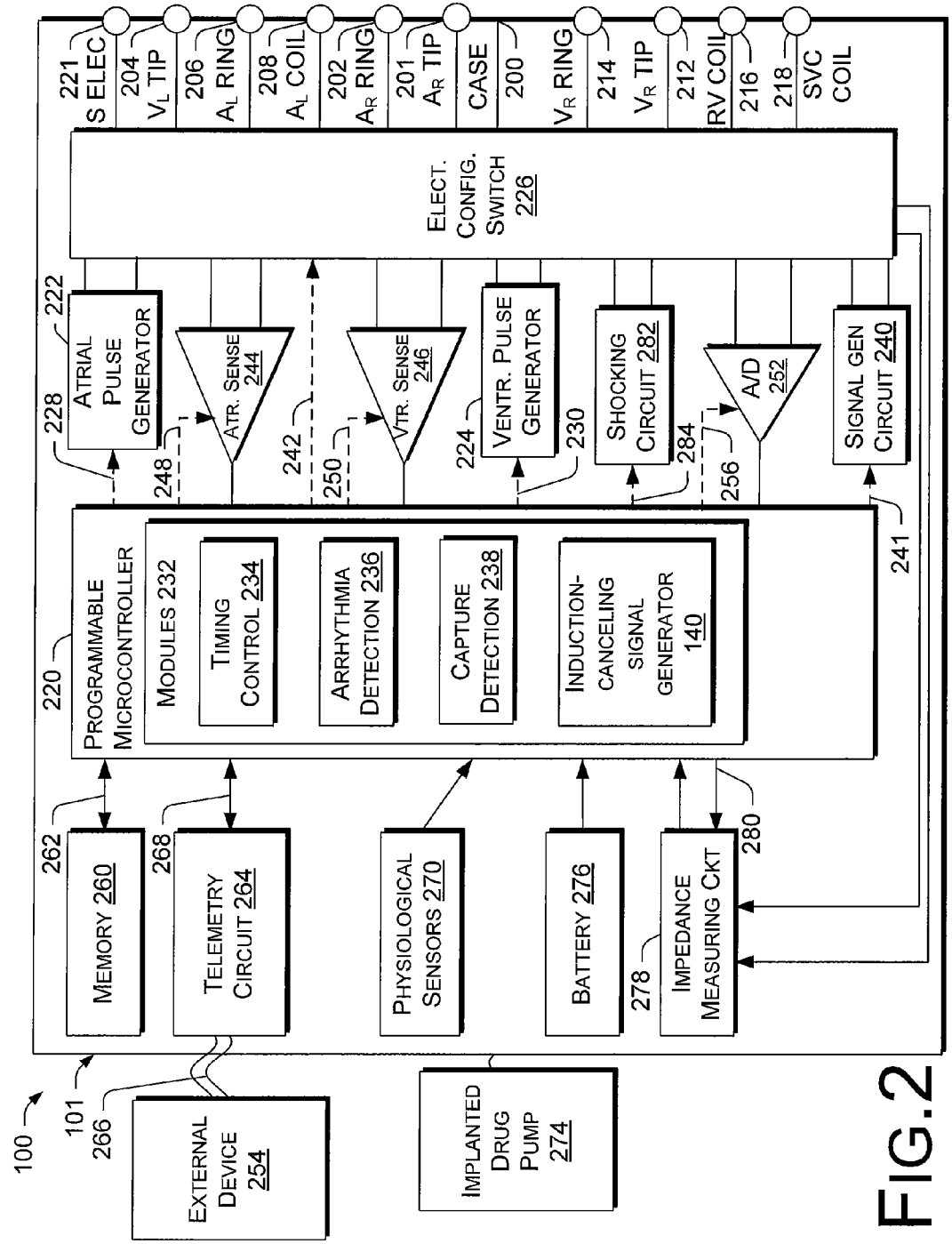
FIG. 2 is a functional block diagram of an exemplary implantable medical device (IMD) illustrating basic elements or features that are operable to address imaging and/or charge induction in accordance with one implementation.

FIG. 2 shows an exemplary, simplified block diagram depicting various components of IMD 100. The IMD 100 can be capable of treating both fast and slow arrhythmias with stimulation therapy, including cardioversion, defibrillation, and pacing stimulation. The IMD can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable IMD. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 200 provides protection to the control unit 101 of IMD 100. The housing is often referred to as the "can", "case" or "case electrode", and may be programmably selected to act as the return electrode for "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 201 adapted for connection to the atrial tip electrode 120. A right atrial ring terminal ($A_R$ RING) 202 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the IMD 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller(s) 220 may be used that carries out the functions described herein. The use of microprocessor-based control circuits for performing timing and data analysis functions are well known in the art.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes a plurality of modules 232 that, when executed, perform various functions of the IMD. For instance, the modules can perform arrhythmia detection, timing control, and/or morphology detection, among other functionalities.

The illustrated example specifically designates a timing control module 234, an arrhythmia detection module 236, a capture detection module 238, and an induction-canceling signal generator (ICSG) module 140.

Timing control module 234 controls the timing of the stimulation pulses (e.g., pacing rate, atrio-ventricular (AV) delay, atrial interconduction (A-A) delay, or ventricular interconduction (VV) delay, etc.) as well as to keep track of the timing of refractory periods, blanking intervals, noise detection windows, evoked response windows, alert intervals, marker channel timing, etc., which is well known in the art.

The arrhythmia detection module 236 and the capture detection module 238 can be utilized by the IMD 100 for detecting patient conditions and determining desirable times to administer various therapies such as pacing, defibrillation and/or in vivo dispensing of pharmaceuticals.

The induction-canceling signal generator (ICSG) module 140 is operable to determine that a patient is being exposed to, or is about to be exposed to, a strong magnetic field and/or rf pulses associated with magnetic resonance imaging (MRI). In some scenarios, the ICSG 140 determines that the patient is going to be exposed to a magnetic field and/or rf pulse by receiving a signal from an external device that indicates that the patient is going to undergo magnetic resonance imaging. For instance, a clinician may send the signal via a programmer or IMD device manager prior to imaging. In another scenario, the ICSG can include or be coupled to a sensing means for directly or indirectly detecting the presence of a strong magnetic field and/or the rf pulse associated with an MRI. For example, the ICSG can sense the magnetic field and/or rf pulses. Alternatively or additionally, the ICSG can sense affects of the MRI. For instance, the ICSG can sense an unexpected charge on conductors of one or more of leads 104-110 where the charge may be indicative of the MRI process. In one implementation, the sensing can be accomplished via atrial and/or ventricular sensing circuits (introduced below). The ICSG 140 then obtains and analyzes the detected signals to detect magnetically or rf induced signals or signal components.

Responsive to determining that the IMD is being exposed to (or is about to be exposed to) a condition associated with an MRI, the ICSG 140 can generate a signal effective to reduce or cancel charge induced upon a lead of the IMD by the MRI. In one case, the ICSG causes one or both of the atrial and ventricular pulse generators 222, 224 to generate the signal for cancelling induced charge on the leads. In another instance the ICSG 140 causes the cancelling signal to be generated by a dedicated signal generating circuit 240 via a control signal 241.

The aforementioned modules 232 may be implemented in hardware as part of the microcontroller 220, or as software/firmware instructions programmed into the device and executed on the microcontroller 220 during certain modes of operation, or the functionality of a module can be accomplished via a free standing hardware component of the IMD, such as an application specific integrated chip (ASIC).

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers.

Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the IMD 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, IMD 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 236 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy.

Advantageously, the operating parameters of the IMD 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The IMD 100 can further include a physiologic sensor(s) 270 to detect one or more of patient activity, patient posture, and respirations, among others. Microcontroller 220 can utilize data received from the physiologic sensor(s) 270 to adjust the various pacing parameters (such as rate, AV Delay, VV Delay, etc.) at which the atrial and ventricular pulse generators, 222 and 224, generate stimulation pulses.

While shown as being included within the IMD 100, it is to be understood that the physiologic sensor 270 may also be external to the IMD 100, yet still be implanted within or carried by the patient. Examples of physiologic sensors that may be implemented in IMD 100 include known sensors that, for example, sense pressure, respiration rate, pH of blood, cardiac output, preload, afterload, contractility, oxygen levels, and so forth.

The physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's posture and activity status, such as whether the patient is climbing upstairs or descending downstairs or whether the patient is sitting up after lying down.

The IMD 100 optionally includes circuitry capable of sensing heart sounds and/or vibration associated with events that produce heart sounds. Such circuitry may include an accelerometer as conventionally used for patient position and/or activity determinations.

While an accelerometer may be included in the case of an IMD in the form of an implantable pulse generator device, alternatively, an accelerometer communicates with such a device via a lead or through electrical signals conducted by body tissue and/or fluid. In the latter instance, the accelerometer may be positioned to advantageously sense vibrations associated with cardiac events. For example, an epicardial accelerometer may have improved signal to noise for cardiac events compared to an accelerometer housed in a case of an implanted pulse generator device.

IMD 100 may also include, or be in communication with, an implanted drug pump 274 or other drug delivery mechanism to effect patient therapy.

The IMD 100 additionally includes a battery 276 that provides operating power to all of the circuits shown in FIG. 2. For the IMD 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The IMD 100 can further include magnet detection circuitry (not shown), coupled to the microcontroller 220, to detect when a magnet is placed over the IMD 100. A magnet may be used by a clinician to perform various test functions of the IMD 100 and/or to signal the microcontroller 220 that the external programmer 254 is in place to receive or transmit data to the microcontroller 220 through the telemetry circuits 264.

The IMD 100 further includes an impedance measuring circuit 278 that is enabled by the microcontroller 220 via a control signal 280. Uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance, such as for determining shock thresholds, (HF indications—pulmonary edema and other factors); detecting when the device has been implanted; measuring stroke volume; and detecting the opening of heart valves, etc. The impedance measuring circuit 278 is advantageously coupled to the switch 226 so that any desired electrode may be used.

In the case where the IMD 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses in a range of joules, for example, conventionally up to about 40 J, as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize battery drain and the more rapid delivery of the shock if the lower energy levels are effective in restoring a normal rhythm), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In low-energy cardioversion, an IMD typically delivers a cardioversion stimulus (e.g., 0.1-5 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the IMD initiates defibrillation therapy.

While an IMD may reserve defibrillation as a latter tier therapy, it may use defibrillation as a first-tier therapy for VF. In general, an IMD does not synchronize defibrillation therapy with any given portion of a ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two current pathways.

First Exemplary Lead

Figure 3:
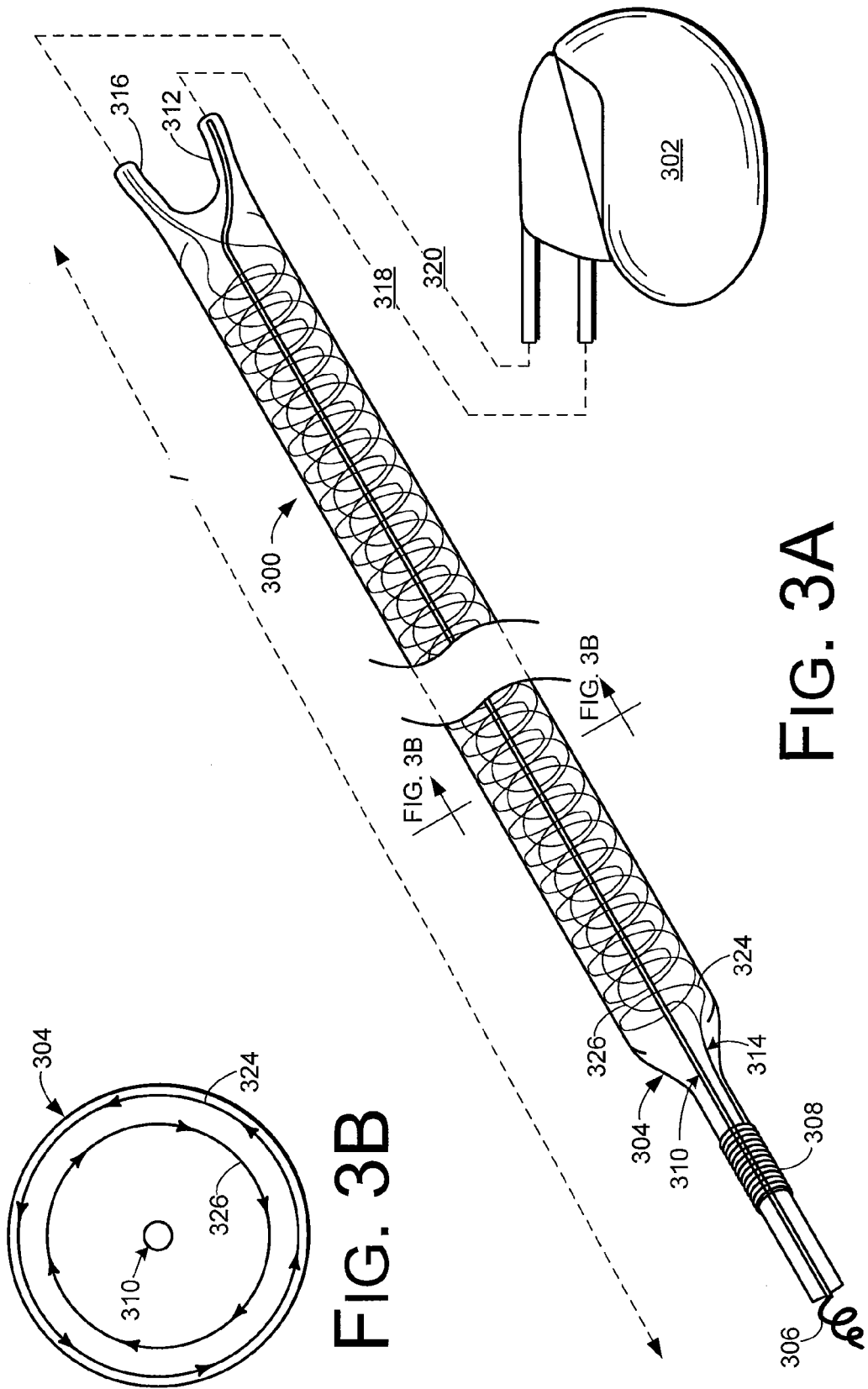
FIG. 3A is a perspective view of an exemplary IMD configured to address imaging and/or charge induction in accordance with various implementations.
FIG. 3B is a sectional view of the IMD of FIG. 3A.

FIGS. 3A-3B illustrate an IMD 300 that includes a control unit 302 and a flexible lead 304 that addresses charge induction. Lead 304 extends along a length/between two electrically isolated electrodes 306, 308 and control unit 302. In this instance, electrode 306 is a tip electrode for embedding in patient tissue and electrode 308 is a ring electrode positioned less proximate the tip.

Lead 304 provides a first conductive pathway 310 that functions to deliver cardiac-related signals between tip electrode 306 and a first connector 312. Lead 304 also provides a second induction-cancelling conductive pathway 314 that functions to deliver cardiac-related signals between ring electrode 308 and a second connector 316. The first and second connectors 312, 316 are configured to electrically couple to control unit 302 as indicated via dashed lines 318, 320 respectively. In the illustrated configuration first conductive pathway 310 is formed from a conductive cable, but other implementations can alternatively or additionally be formed from a conductive coil and/or any other suitable mechanism or combination of mechanisms. Second induction-cancelling conductive pathway 314 includes two counter-wound or counter-rotational conductive spiral coils 324, 326 (as may be appreciated from FIG. 3B). Stated another way, one of conductive coils 324, 326 is a right-hand coil while the other of conductive coils 324, 326 is a left-hand coil. Conductive coils 324, 326 are coincident with first conductive pathway 310. In this particular instance, conductive coils 324, 326 are coaxial with first conductive pathway 310.

Conductive coils 324, 326 are inter-connected at the ring electrode 308 and second connector 316 to provide electrically parallel paths along the second conductive pathway 314. In some configurations, conductive coils 324, 326 can be electrically isolated from one another between the ring electrode 308 and second connector 316. In other configurations the conductive coils 324, 326 can be in electrical contact at one or more intervening points between the ring electrode 308 and second connector 316.

Upon exposure to a magnetic resonance imaging process any charge induced on conductive coil 324 is generally offset or cancelled by a similar but opposite charge that is induced upon conductive coil 326 due to the counter-wound nature of the two coils 324, 326. Assume for purposes of example that exposure to the magnetic resonance imaging process causes an induced charge to flow along coil 324 from connector 316 to ring electrode 308. The magnetic resonance imaging process would also induce a similar charge to flow in the opposite direction along coil 326 (i.e., from electrode 308 to connector 316). The net result of the two induced currents is essentially no (or at least reduced) overall induced charge in the target tissue proximate ring electrode 308. Accordingly, second induction-cancelling conductive pathway 314 offers an example of an induction-cancelling cardiac-signal delivery pathway. Stated another way, second induction-cancelling conductive pathway 314 can deliver cardiac-related signals from control unit 304 to a target tissue proximate ring electrode 308 while reducing or eliminating unintended charge delivery to the target tissue that may inappropriately stimulate the target tissue when the patient is exposed to the magnetic resonance imaging process. Further, conductive coils 324, 326 can serve to shield the first conductive pathway 310 from charge induction upon exposure to magnetic resonance imaging, thereby reducing inadvertent stimulation of patient tissue proximate electrode 306. The skilled artisan should recognize other implementations. For instance, the first conductive pathway 310 can include counter-wound coils similar to those described in relation to the second conductive pathway 314 such that any induced charge on the first conductive pathway is self-cancelling.

Second Exemplary Lead

Figure 4:
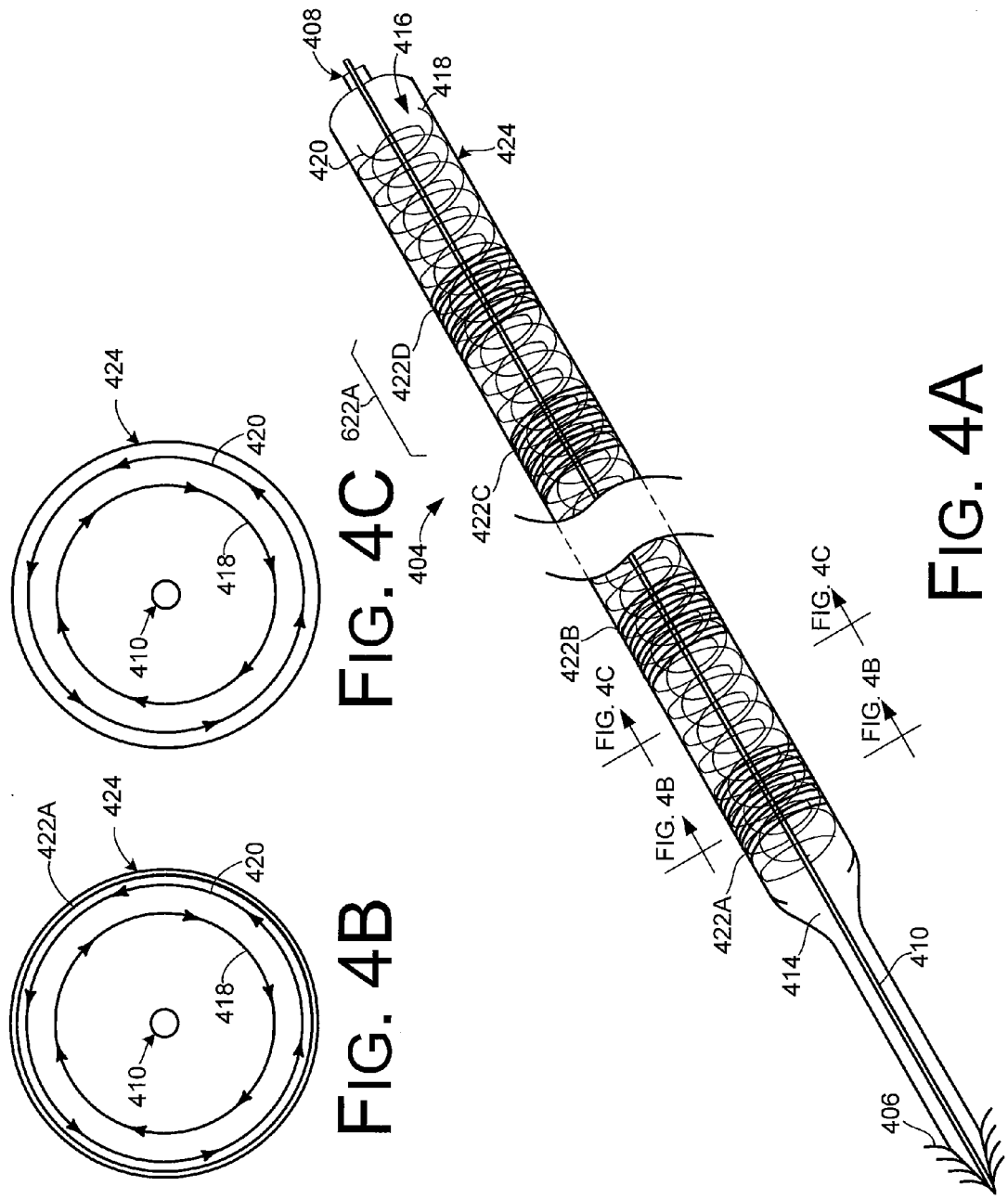
FIG. 4A is a perspective view of an exemplary IMD configured to address imaging and/or charge induction in accordance with various implementations.
FIGS. 4B and 4C are sectional views of the IMD of FIG. 4A.

FIGS. 4A-4C illustrate another flexible lead 404 configured to address charge induction and/or imaging considerations. Lead 404 is operable to extend between an electrode 406 and a connector 408 for connecting to a control unit (not shown). Lead 404 provides a conductive pathway 410 that functions to deliver cardiac-related signals between electrode 406 and connector 408. In the illustrated configuration, conductive pathway 410 is formed from a conductive cable, but other implementations can alternatively or additionally be formed from a conductive coil(s) and/or any other suitable mechanism or combination of mechanisms. An insulative material 414 protects conductive pathway 410 from damage. An induction-cancelling mechanism 416 surrounds and shields conductive pathway 410 for at least a portion of its length. In this instance, a majority of conductive pathway 410 is surrounded by induction-cancelling mechanism 416 effective that only distal portions of the conductive pathway 410 proximate electrode 406 and connector 408 are unshielded. In this case, induction-cancelling mechanism 416 includes first and second oppositely wound coils 418, 420 that are electrically isolated from conductive pathway 410. First and second oppositely wound coils 418, 420 can be thought of as providing self-cancelling inductive shielding to conductive pathway 410 in that charge induction on the coil 418 tends to be cancelled by charge induction on coil 420.

Lead 404 also includes an imaging-related mechanism in the form of imaging coils 422A, 422B, 422C, and 422D interposed between electrode 406 and connectors 408. In this case, the imaging coils are electrically insulated from coils 418, 420 by insulative material 414. Further, the imaging coils are embedded in the insulative material sufficiently that the imaging coils are not exposed through an outer surface 424 of the insulative material. Various properties associated with imaging coils 422A, 422B, 422C, and 422D can be varied to enhance imaging of lead 404 in various magnetic imaging scenarios. Examples of these properties can include a pitch of the windings of the imaging coils, a length of the imaging coils, and/or a distance between individual imaging coils. These properties are discussed in more detail below in relation to FIG. 8.

In this implementation the first and second oppositely wound coils 418, 420 are embedded in insulative material 414 such that coils 418, 420 are electrically insulated from conductive pathway 410 by insulative material 414. Also, in this configuration, the oppositely wound coils 418, 420 are electrically insulated from the imaging coils 422A-422D. Both of oppositely wound coils 418, 420 and the imaging coils 422A-422D are covered by insulative material 414 so as not to be exposed on an outer surface 424 of lead 404. In other configurations, oppositely wound coils 418, 420 and the imaging coils 422A-422D can be electrically connected rather than insulated from one another. Further, in some configurations, portions of the oppositely wound coils 418, 420 and/or the imaging coils 422A-422D can be exposed through the outer surface 424 at predetermined locations. Exposing portions of oppositely wound coils 418, 420 and/or the imaging coils 422A-422D at the predetermined locations can allow MRI induced heat and/or charge dissipation where little or no damage to patient tissues may occur. For instance, the predetermined locations can be selected so that when lead 404 is implanted in the patient the predetermined locations are proximate areas of high blood volume and/or perfusion. For example, exposing the coils 418, 420 in a location on the lead that is predetermined to extend along the patient's superior vena cava can allow blood volume and blood flow to reduce any risk of tissue damage associated with induced charge and/or heat.

The conductive pathway, induction-cancelling mechanism, and the imaging-related mechanisms can be formed from any conductive materials such as copper or steel. Various corrosion resistant steels or stainless steels such as MP35N can be employed in some implementations.

Third Exemplary Lead

Figure 5:
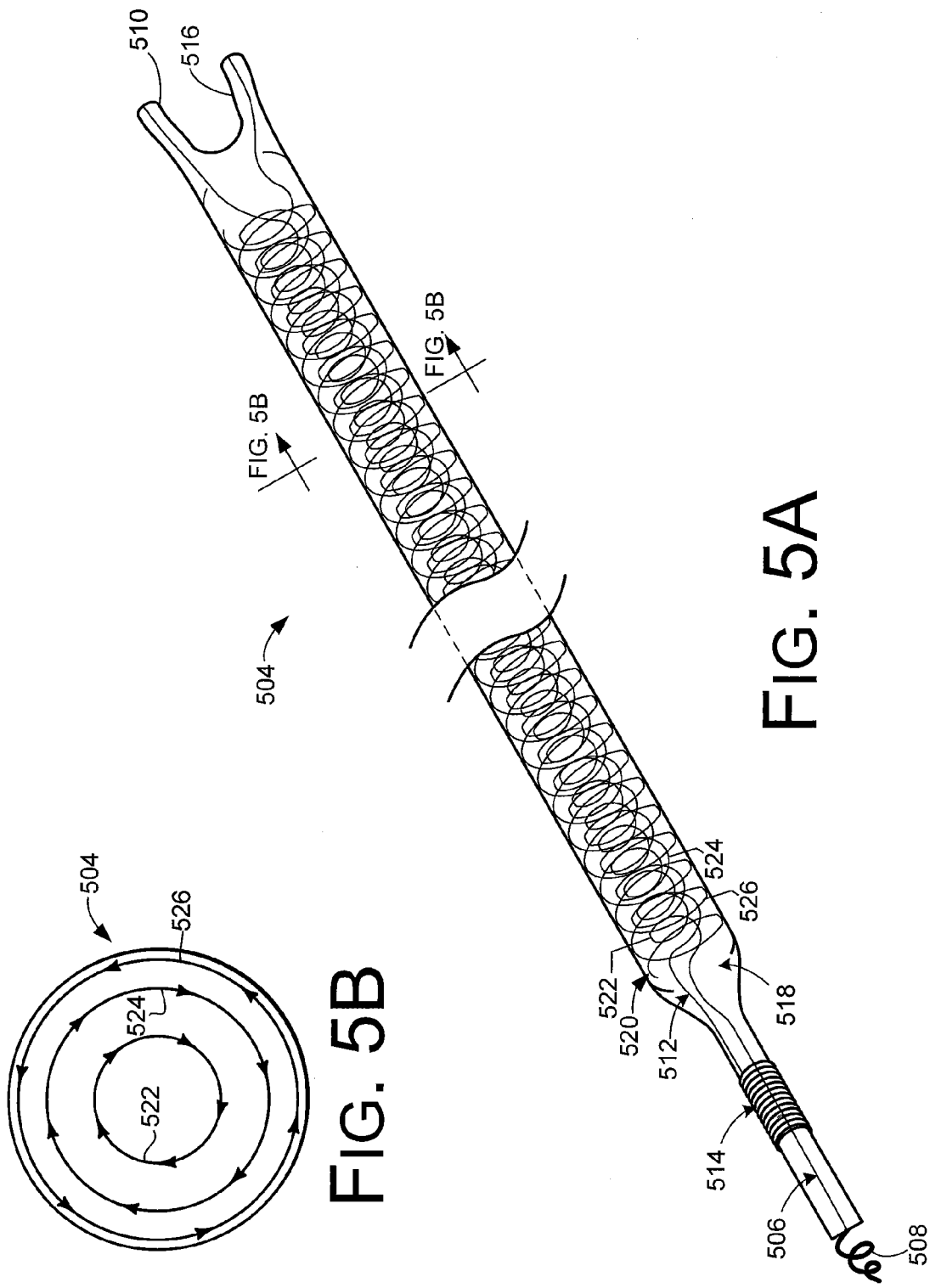
FIG. 5A is a perspective view of an exemplary IMD configured to address imaging and/or charge induction in accordance with various implementations.
FIG. 5B is a sectional view of the IMD of FIG. 5A.

FIGS. 5A-5B illustrate another lead 504 configured to address charge induction. Lead 504 contains a first conductive pathway 506 between a tip electrode 508 and a first connector 510 and a second conductive pathway 512 extending between a ring electrode 514 and second connector 516. An insulative material 518 protects the first and second conductive pathways from damage. An induction-cancelling mechanism 520 surrounds a portion of the first and second conductive pathways. In this instance, first conductive pathway 506 includes a first conductive coil 522 that is connected to tip electrode 508 and first connector 510. Similarly, second conductive pathway 512 includes a second conductive coil 524 that is connected to ring electrode 514 and second connector 516. Induction-cancelling mechanism 520 includes a third coil 526. In this instance each of the three coils (522, 524, and 526) are electrically isolated from one another.

Figure 6:
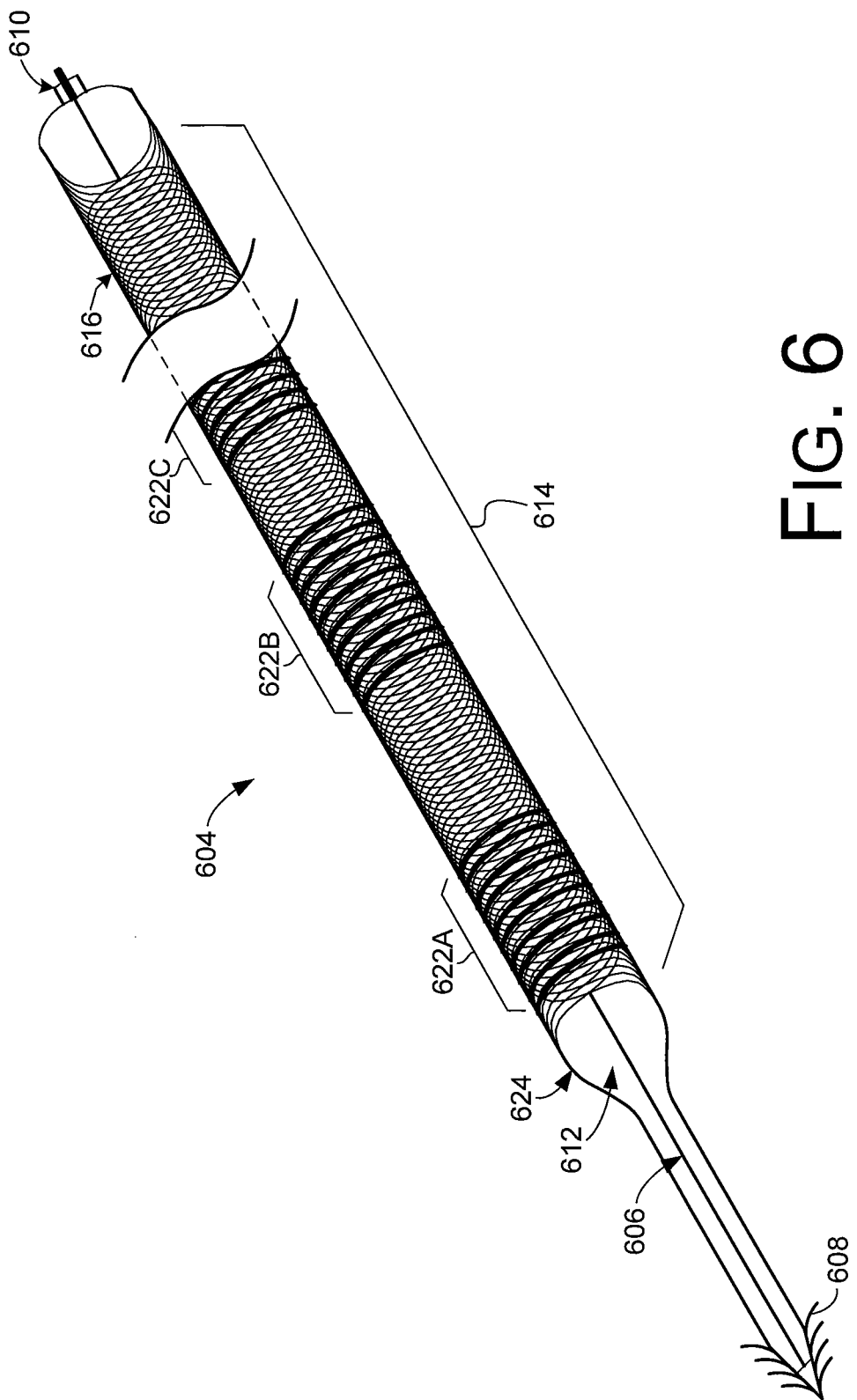
FIG. 6 is a perspective view of an exemplary IMD configured to address imaging and charge induction in accordance with various implementations.

In the illustrated implementation, the first and second coils 522, 524 share a common winding that is opposite from a winding of the third coil 526. For instance, if the first and second coils have right-hand windings then the third coil 526 has a left-hand winding and conversely if the first and second coils have left-hand windings then the third coil has a right-hand winding. In this case the third coil offers electromagnetic shielding to the first and second coils. Further, the opposite winding of the third coil relative to the first and second coils offers an inductive cancelling affect to both the first and second coils. Accordingly, the third coil of the induction-cancelling mechanism reduces magnetically induced affects on the first and second conductive pathways. Imaging mechanisms, such as the imaging coils described above in relation to FIG. 4 can also be employed on lead 504. The imaging coils can be tuned to enhance imaging of lead 504. The imaging coils can be electrically isolated from coil 526 or electrically coupled to coil 526. The imaging coils can be embedded in insulative material 518 and/or can be exposed to dissipate charge and/or heat at desired locations within the patient such as where rapid high-volume blood perfusion can readily dissipate heat and/or charge. The skilled artisan should recognize other configurations consistent with the concepts described above and below, Fourth Exemplary Lead FIG. 6 illustrates a flexible lead 604 that has both induction-reducing and image-enhancing features. Lead 604 includes a conductive pathway 606 extending between an electrode 608 and a connector 610. An insulative material 612 surrounds conductive pathway 606. An imaging-related mechanism 614 is positioned upon insulative material 612. In this instance the imaging-related mechanism 614 includes a conductive braid 616 and a plurality of conductive imaging coils 622A, 622B, and 622C. Conductive braid 616 reduces charge induction upon conductive pathway 606 when lead 604 is exposed to magnetic resonance imaging. Individual imaging coils 622A, 622B, and 622C can also reduce charge induction and can further provide enhanced imaging resolution of lead 604 in a magnetic resonance image. As mentioned above in relation to FIG. 4 and as will be described in more detail below, properties associated with imaging coils 622A-622C can be tuned to a particular MRI configuration to enhance imaging of lead 604.

In some instances, the imaging coils 622A-622C and braid 616 are embedded in and electrically isolated by insulative material 612. In other instances, one or more of the imaging coils can be electrically exposed through an outer surface 624 of insulative material 612 at predetermined positions. In some such configurations, the exposed imaging coils can function as energy sinks that dissipate charge into the patient's body in a manner that reduces any associated localized heating and/or charge induction of target tissue proximate electrode 608. For instance, the predetermined regions can be selected to ultimately be positioned in regions of the patient's vasculature where blood flow will reduce heat build-up proximate the exposed imaging coils.

Fifth Exemplary Lead

Figure 7:
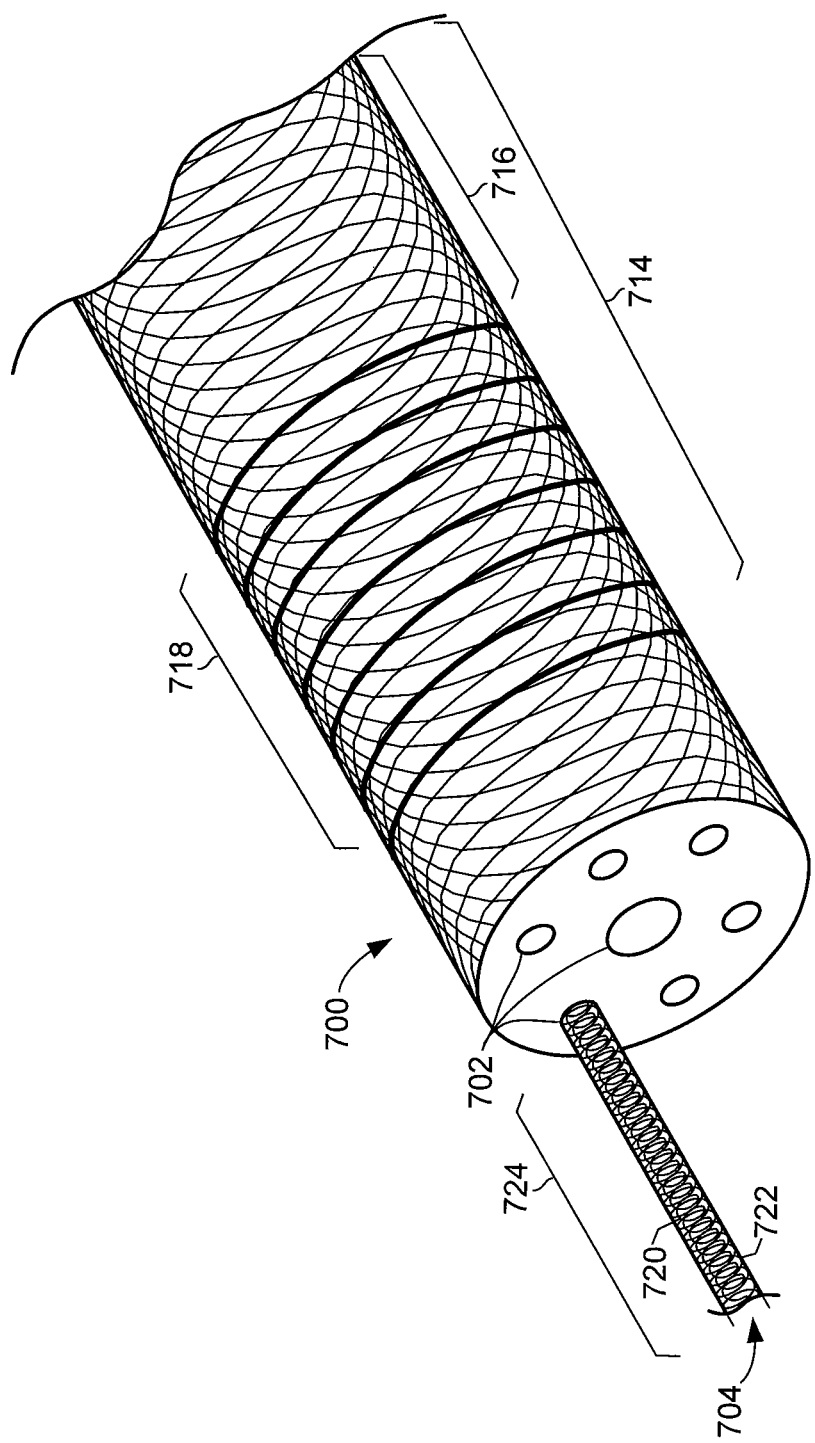
FIG. 7 is a perspective view of an exemplary IMD configured to address imaging and/or charge induction in accordance with various implementations.

FIG. 7 illustrates a multi-lumen lead 700 that defines a multitude of lumens or tubes 702 (not all of which are designated with specificity). Individual leads, such as lead 704 can be inserted or otherwise contained in individual lumens 702. The induction-reducing and image-enhancing concepts described above can be employed to one or both of multi-lumen lead 700 and leads 704. In the illustrated configuration, multi-lumen lead 700 is employing an imaging-related mechanism 714 similar to the imaging-related mechanism described above in relation to FIG. 6. The imaging-related mechanism 714 includes a conductive braid 716 that is electrically coupled to conductive coil(s) 718. Conductive braid 716 can reduce charge induction upon leads passing through the lumens. For instance, the conductive braid can reduce charge induction on lead 704 passing through lumen 702A. Conductive coil 718 can further reduce charge induction upon lead 704 and can enhance imaging of lead 700. Further still, in this instance, lead 704 is employing oppositely-wound coils 720, 722 to create a self-cancelling conductive pathway 724. Shielding and/or imaging enhancing mechanisms can alternatively or additionally be employed on individual leads such as lead 704 passing through lumen 702 to enhance imaging of the individual leads and/or to diminish negative consequences of the imaging upon the patient.

Sixth Exemplary Lead

Figure 8:
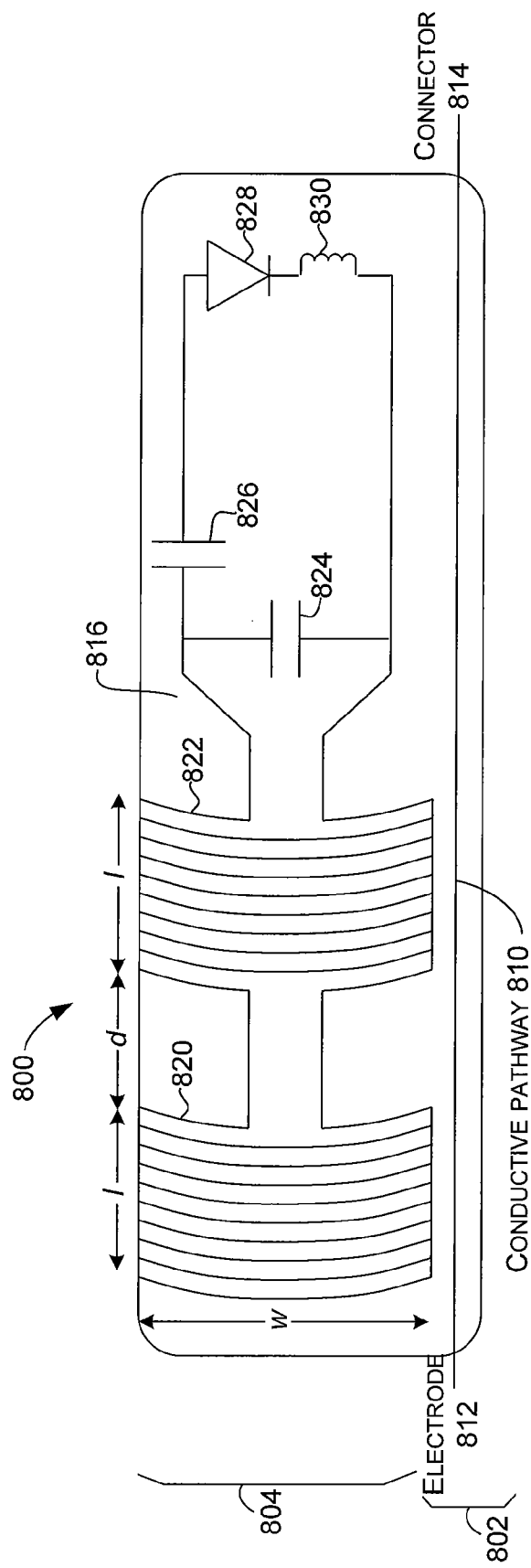
FIG. 8 is a schematic representation of an exemplary IMD configured to address imaging and/or charge induction in accordance with various implementations.

FIG. 8 illustrates a schematic representation of an image-enhancing lead 800. In this case lead 800 includes a signal delivery circuit 802 and an image enhancing circuit 804. Signal delivery circuit 802 functions to deliver signals between a target tissue and a control unit of an IMD. Signal delivery circuit 802 includes a conductive pathway 810 extending between an electrode 812 and a connector 814. An electrically insulative protective material 816 surrounds conductive pathway 810 and image enhancing circuit 804. As mentioned above, in other implementations some image enhancing components can be exposed through the protective material.

In this case, image enhancing circuit 804 includes two image enhancing coils 820, 822, two capacitors 824, 826, a pin diode 828, and a choke 830. Starting arbitrarily at the diode 828, the diode's cathode is connected to a first side of choke 830. A first side of coils 820, 822 and first capacitor 824 are connected in parallel between the second side of choke 830 and a first side of the second capacitor 826. The second side of the second capacitor 826 is connected to the anode of the diode 828 to complete the circuit.

Image enhancing circuit 804 can be tuned to various magnetic resonance imaging configurations. For instance, in this case, coils 820, 822 have a length/in range from about 3 millimeters to about 4 millimeters and a diameter or width w in a range from about 1.5 millimeters to about 3 millimeters. A distance d between coils 820, 822 is in a range from about 20 millimeters to about 40 millimeters. (FIG. 8 is not illustrated to scale). In one instance, distance d is set at 23 millimeters for a 63.6 megahertz MRI. Further, imaging circuit 804 can be tuned and matched to the receive channels of an expected MRI via capacitors 824, 826 and/or diode 828. For example, in the case of a three tesla MRI at 64 megahertz or 128 megahertz, the capacitors 824, 826 collectively provide a capacitance in a range from about 500 to about 700 picofarads. Another configuration for use with a 0.5 tesla MRI at 21 megahertz can utilize a 220 Pico farad capacitor 824 and a 150 picofarad capacitor 822. Accordingly, in both configurations the capacitors contribute to a small frequency dependent load at an expected MRI frequency.

Stated another way, from a functional standpoint, the coils 820, 822 of the image enhancing circuit mimic a loop antenna, and thereby create small regions with a high signal-to-noise ratio for the receiving channels of the MRI. Accordingly, the image enhancing circuit of FIG. 8 offers but one possible circuit configuration for achieving image enhancement in an MRI environment. For example, capacitor 824 can be eliminated and/or replaced by a single or back-to-back diodes in other implementations. In another case, the turns of the coil can be adjusted to the Larmor frequency of the intended MRI environment, where the Larmor frequency is the frequency at which a magnetic nucleus comes into resonance in a magnetic field of given strength.

In the illustrated implementation, all of the components 820-830 of image enhancing circuit 804 are illustrated contained within lead 800, however, such need not be the case. For instance, in other implementations some or all of capacitors 824, 826, diode 828 and/or choke 830 can be positioned within a control unit of the IMD for electrical connection to the components (i.e., coils 820, 822) positioned on the lead. Contrastingly, other implementations can employ a "device-less lead" that incorporates some or all of the functionality of a control unit and a lead in a single integrated device rather than employing distinct leads and control units. The skilled artisan should recognize other variations consistent with these concepts.

CONCLUSION

The IMD imaging and charge induction concepts described herein enhance resolution of magnetic resonance images for patients having IMDs while reducing or eliminating deleterious heating and charge induction caused by the imaging process.

Although exemplary techniques, methods, devices, systems, etc., have been described in language specific to structural features and/or methodological acts, it is to be understood that the subject matter defined in the appended claims is not limited to the specific features or acts described. Rather, the specific features and acts are disclosed as exemplary forms of implementing the claimed methods, devices, systems, etc.

What is claimed is:

1. A lead for use with an implantable medical device comprising:
   first and second electrodes operable to be positioned in electrical communication with a target tissue of a patient;
   a connector operable to be electrically coupled to the implantable medical device;
   first and second conductors operable to conduct signals between the first electrode and a first contact of the connector, at least a portion of the first conductor comprising a right-hand coil and at least a portion of the second conductor comprising a left hand coil that is coextensive with the first conductor right-hand coil portion; and
   a third conductor operable to conduct signals between the second electrode and a second contact of the connector, wherein the right-hand coil portion of the first conductor and the coextensive left-hand coil portion of the second conductor surround a portion of the third conductor, wherein the portion of the first conductor and the portion of the second conductor are co-axial with the third conductor.

2. The lead of claim 1, wherein the at least a portion of the first conductor surrounds the at least a portion of the second conductor.

3. The lead of claim 1, wherein the at least a portion of the second conductor surrounds the at least a portion of the first conductor.

4. The lead of claim 1, wherein the first and second conductors are distinct between the electrode and the connector.

5. The lead of claim 1, wherein the first and second conductors are incident along a third portion.

6. The lead of claim 1, wherein the portion of the first conductor and the portion of the second conductor extend entirely between the electrode and the connector.

7. The lead of claim 1, further comprising a multi-lumen lead body and wherein the first conductor and the second conductor extend through an individual lumen of the multi-lumen lead body.

8. The lead of claim 1, further comprising a fourth conductor parallel to the third conductor and electrically isolated from the first and second conductors and operable to conduct signals between the second electrode and the second contact of the connector, at least a portion of the third conductor comprising a right-hand coil and at least a portion of the fourth conductor comprising a left hand coil that is coextensive with the third conductor.

* * * * *